(12) United States Patent
Pittenger et al.

(10) Patent No.: US 8,852,572 B2
(45) Date of Patent: *Oct. 7, 2014

(54) CARDIAC MUSCLE REPAIR OR REGENERATION USING BONE MARROW-DERIVED STEM CELLS

(75) Inventors: Mark F. Pittenger, Severna Park, MD (US); Stephen L. Gordon, Columbia, MD (US); Alastair Morgan Mackay, Towson, MD (US)

(73) Assignee: Mesoblast International Sarl (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,009

(22) Filed: Feb. 9, 2012

(65) Prior Publication Data

US 2012/0141438 A1 Jun. 7, 2012

Related U.S. Application Data

(63) Continuation of application No. 12/725,867, filed on Mar. 17, 2010, now Pat. No. 8,158,120, which is a continuation of application No. 12/395,949, filed on Mar. 2, 2009, now Pat. No. 7,892,829, which is a continuation of application No. 10/690,435, filed on Oct. 21, 2003, now Pat. No. 7,514,074, which is a continuation-in-part of application No. 10/278,148, filed on Oct. 22, 2002, now abandoned, which is a continuation-in-part of application No. 10/127,737, filed on Apr. 22, 2002, now abandoned, which is a continuation of application No. 09/446,952, filed as application No. PCT/US98/14520 on Jul. 14, 1998, now Pat. No. 6,387,369.

(60) Provisional application No. 60/052,910, filed on Jul. 14, 1997.

(51) Int. Cl.
*A61K 48/00* (2006.01)
*C12N 15/85* (2006.01)

(52) U.S. Cl.
USPC .......................................... 424/93.1; 435/325

(58) Field of Classification Search
USPC .......................................... 424/93.1; 435/325
See application file for complete search history.

(56) References Cited

U.S. PATENT DOCUMENTS

| | | | |
|---|---|---|---|
| 5,226,914 A | 7/1993 | Caplan et al. |
| 5,486,359 A | 1/1996 | Caplan et al. |
| 5,591,625 A | 1/1997 | Gerson et al. |
| 5,716,616 A | 2/1998 | Prockop et al. |
| 5,846,796 A | 12/1998 | Cerami et al. |
| 6,099,832 A | 8/2000 | Mickle et al. |
| 6,387,369 B1 | 5/2002 | Pittenger et al. |
| 7,015,037 B1 | 3/2006 | Furcht et al. |
| 7,514,074 B2 | 4/2009 | Pittenger et al. |
| 8,075,881 B2 | 12/2011 | Verfaillie et al. |
| 8,486,696 B2 | 7/2013 | Ho et al. |
| 2007/0003530 A1 | 1/2007 | Pittenger et al. |

FOREIGN PATENT DOCUMENTS

| | | |
|---|---|---|
| WO | 94/00484 | 1/1994 |
| WO | 96/30031 | 10/1996 |
| WO | 99/03973 | 1/1999 |
| WO | 00/06701 | 7/1999 |
| WO | 99/49015 | 9/1999 |
| WO | 0017326 | 3/2000 |
| WO | 2004/084921 | 10/2004 |

OTHER PUBLICATIONS

Barbash et al (Circulation, 108: 863-868, 2003).*
Pittenger et al (Circ Res, 95: 9-20, 2004).*
Breitbach et al., Blood, 110:1362-1369 (2007).
Bruder et al., Mesenchymal Stem Cells in Bone Development, Bone Repair, and Skeletal Regeneration Therapy, J. Cell. Biochem., 56:283-294 (1994).
Chen et al., Stroke, 32:1005-1011 (2001).
Chen, J. Neurol. Sci., 189:49-57 (2001).
Chiu et al., Ann. Therac. Surg., 60:12-18 (1995).
Chopp et al., The LANCET Neurology, 1:92-100 (2002).
Dalton et al., J. Cell. Biochem., Supp. 17E, Abstract R 202 (1993).
Deisher et al., U.S. Appl. No. 60/079,132.
European Search Report corresponding to European Patent Application Serial No. 03776501.3-1222, dated Oct. 19, 2009.
Galinanes et al., Cell Transplantation, 13:7-13 (2004) (Abstract).
Gerson, Nature Med., 5:262-264 (1999).
Grigoriadis et al., Differentiation of Muscle, Fat, Cartilage, and Bone from Progenitor Cells Present in a Bone-derived Clonal Cell Population: Effect of Dexamethasone, J. Cell Biol., 106:2139-2151 (1988).
International Preliminary Examination Report in PCT/US98/14520, dated Sep. 3, 1999.
International Search Report in PCT/US98/14520, dated Oct. 13, 1998.
Jorgensen et al., Curr. Opin. Biotechnol., 15:406-410 (2004).
Kassem, Cloning and Stem Cells, 6(4):369-375 (2004).
Klug et al., Genetically Selected Cardiomyocytes from Differentiating Embroyonic Stem Cells from Stable Intracardiac Grafts, J. Clin. Invest., 98(1):216-224 (1996).
Krebsbach et al., Bone Formation in Vivo: Comparison of Osteogenesis by Transplanted Mouse and Human Marrow Stromal Fibroblasts, Transplantation, 63:1059-1069 (1997).
Lee et al., Ann. Intern. Med., 140:729-737 (2004).
Li et al., Neurology, 59:514-523 (2002).

(Continued)

Primary Examiner — Marcia S Noble
Assistant Examiner — Magdalene Sgagias
(74) Attorney, Agent, or Firm — McAndrews, Held & Malloy, Ltd

(57) ABSTRACT

Disclosed are compositions and methods for repairing and/or regenerating cardiac tissue by administering adult bone marrow-derived stem cells to an individual. These cells can be administered as a liquid injectible or as a preparation of cells in a matrix which is or becomes solid or semi-solid. The cells can be genetically modified to enhance myocardial differentiation and integration. Also disclosed is a method for replacing cells ex vivo in a heart valve for implantation.

15 Claims, 8 Drawing Sheets

(56) References Cited

OTHER PUBLICATIONS

Lin et al., Natural Killer Cell- and Macrophage-Mediated Rejection of Concordant Xenografts in the Absence of T and B Cell Responses, J. Immunol., pp. 5658-5667 (1997).
Martin et al., "Allogeneic mesenchymal stem cell engraftment in the infracted rat heart: Timing and delivery route." Bone Marrow Transplantation, vol. 29, No. S2, Mar. 2002, XP002549207.
Minguell et al., Exp. Biol. Med., 226:507-520 (2001).
Office Action in U.S. Appl. No. 09/446,952, dated Jan. 18, 2001.
Office Action in U.S. Appl. No. 09/446,952, dated Jun. 6, 2000.
Office Action in U.S. Appl. No. 10/690,435, dated Aug. 18, 2008.
Office Action in U.S. Appl. No. 10/690,435, dated Jan. 12, 2006.
Office Action in U.S. Appl. No. 10/690,435, dated Jan. 29, 2008.
Office Action in U.S. Appl. No. 10/690,435, dated Jul. 17, 2007.
Office Action in U.S. Appl. No. 10/690,435, dated Mar. 22, 2007.
Office Action in U.S. Appl. No. 10/690,435, dated Nov. 3, 2005.
Office Action in U.S. Appl. No. 10/690,435, dated Sep. 22, 2006.
Office Action in U.S. Appl. No. 11/475,568, dated Apr. 3, 2008.
Office Action in U.S. Appl. No. 11/475,568, dated Dec. 12, 2007.
Office Action in U.S. Appl. No. 12/395,949, dated Jan. 12, 2010.
Office Action in U.S. Appl. No. 12/395,949, dated Jun. 22, 2010.
Orkin et al., In Report and Recommendations of the Panel to Assess the NIH Investment in Research on Gene Therapy (1995).
Ott et al., Basic Res. Cardiol., 100:504-517 (2005).
Parmley et al., West J. Med., 154:427-441 (1991).
Pereira et al., Cultured adherent cells from marrow can serve as long-lasting precursor cells for bone, cartilage, and lung in irradiated mice, Proc. Natl. Acad. Sci. USA< 92:4857-4861 (1995).
Pfeffer et al., Circulation, 81:1161-1172 (1990).
Prockop, Science, 276:71-74 (1997).
Ramachandran et al., Plasma Homocysteine and Risk for Congestive Heart Failure in Adults Without Prior Myocardial Infarction, JAMA, 289(10):1251-1257 (2003).
Robinson et al., "Implantation of Skeletal Myoblast—Derived Cells," in Cellular Cardiomyoplasty: Myocardial Repair with Cell Implantation, Kao et al., eds., Landes Bioscience, pp. 81-107 (1997).
Saadi et al., Life Sciences, 62:365-387 (1998).
Saito et al., Tissue Engineering, 1(4):327-343 (1995).
Semedo et al., Transplantation Proceedings, 39:421-423 (2007).
Shake et al., The Annals of Thoracic Surgery, 73:1919-1926 (2002).
Szabolcs et al., Apoptosis of Cardiac Myocytes During Cardiac Allograft Rejection, Circulation, 94(7):1665-1673 (1996).
Verma et al., Nature, 389:239-242 (1997).
Office Action in U.S. Appl. No. 13/012,953, dated Jun. 28, 2011.
Office Action in U.S. Appl. No. 13/012,953, dated Aug. 10, 2011.
Office Action in U.S. Appl. No. 12/725,867, dated Jul. 25, 2011.
Martin et al., Blood, 66:664-672 (1995).
Torre-Amione et al., JACC, 27:1201-1206 (1996).
Nagaya et al., Circulation, 1122:1128-1135 (2005).
Yanagisawa-Miwa et al., Science, 257:1401-1403 (1992).
Auerbach et al., Biology of Endothelial Cells, ed. Jaffe, E. (Nijhoff, Boston) pp. 393-400 (1984).
Risau, PNAS USA, 83:3855-3859 (1986).
Office Action in U.S. Appl. No. 12/725,867, dated May 5, 2011.
Wagers et al., Cell, 116:639-648 (2004).
Wakitani et al., Myogenic Cells Derived from Rat Bone Marrow Mesenchymal Stem Cells Exposed to 5-Azacytidine, Muscle & Nerve, 18(12):1417-1426 (1995).
Warejcka et al., A Population of Cells Isolated from Rat Heart Capable of Differentiating into Several Mesodermal Phenotypes, J. Surg. Res., 62:233-242 (1996).
Written Opinion in PCT/US98/14520, dated Jun. 23, 1999.
Fukuda, "Development of regenerative cardiomyocytes from mesenchymal stem cells for cardiovascular tissue engineering," Artif. Organs, 25(3):187-193 (2001).
Hughes, "Cardiac stem cells," J. Pathol., 197(4):468-478 (2002).
International Search Report in PCT/US03/33450, dated Jan. 28, 2005.
Liechty et al., "Human mesenchymal stem cells engraft and demonstrate site-specific differentiation after in utero transplantation in sheep," Nat. Med., 6(11):1282-1286 (2000).
Min et al., "Effects of co-transplantation of cultured human mesenchymal stem cells plus fetal cardiomyocytes on cardiac function in infarcted pigs," Circulation, 104:11-289 (2001).
Min et al., "Significant improvement of heart function by cotransplantation of human mesenchymal stem cells and fetal cardiomyocytes in postinfarcted pigs," Ann. Thorac. Surg., 74(5):1568-1575 (2002).
Office Action in U.S. Appl. No. 12/725,867, dated Dec. 22, 2011.
Saito et al., "Xenotransplant cardiac chimera: immune tolerance of adult stem cells," Ann. Thorac. Surg., 74:19-24 (2002).
Toma et al., "Human mesenchymal stem cells differentiate to a cardiomyocyte phenotype in the adult murine heart," Circulation, 105(1):93-98 (2002).
Wang et al., "The coronary delivery of marrow stromal cells for myocardial regeneration: Pathophysiologic and therapeutic implications," J. Thorac. Cardiovasc. Surg., 122(4):699-705 (2001).
Office Action in U.S. Appl. No. 13/012,956, dated Jul. 21, 2011.
Office Action in U.S. Appl. No. 13/012,956, dated Sep. 1, 2011.
Roobrouck et al. Stem Cells; 29:871-882 (2011) (p. 874, first paragraph).
Nagaya et al. Am J Physiol Heart Circ Physiol; 287:H2670-H2676 (2004).
Freyman et al. European Heart Journal; 27:1114-1122 (2006).
Dai et al. Circulation; 112:214-223 (2005).
Kim et al. Circulation; 112[suppl I]:1-961-104 (2005).
Amado et al. PNAS; 102(32):11474-11479 (2005).
Van't Hof et al. Cytotherapy; 9(5):477-487 (2007).
Van't Hof et al. In: Stem Cells and Myocardial Regeneration; Chap. 4:45-56, 2007.
Zeng et al. Circulation 115:1866-1875 (2007).

* cited by examiner

CONTROL
8 WKS POST MI
(PIG 20)

INJURED ANT.
LV WALL

ALTO MSC
8 WKS POST MI/MSC
(PIG 18)

INJURED ANT.
LV WALL

*p=0.047 AVG. MAXIMUM VS. BASELINE EF

* p=0.047 MINIMUM VS. BASELINE WMSI

H&E (20x)

DAPI LABELED MSCs

FACTOR 8 RELATED PROTEIN
(VON WILLEBRAND FACTOR)

H&E

DAPI & VEG-F

CARDIAC MUSCLE REPAIR OR REGENERATION USING BONE MARROW-DERIVED STEM CELLS

RELATED APPLICATIONS

This application is a continuation of application Ser. No. 12/725,867, filed on Mar. 17, 2010, which is a continuation of application Ser. No. 12/395,949, filed on Mar. 2, 2009 (now U.S. Pat. No. 7,892,829, issued on Feb. 22, 2011), which is a continuation of application Ser. No. 10/690,435, filed Oct. 21, 2003 (now U.S. Pat. No. 7,514,074, issued on Apr. 7, 2009), which is a continuation-in-part of application Ser. No. 10/278,148, filed Oct. 22, 2002 (now abandoned), which is a continuation-in-part of application Ser. No. 10/127,737, filed Apr. 22, 2002 (now abandoned), which is a continuation of application Ser. No. 09/446,952, filed Mar. 27, 2000 (now U.S. Pat. No. 6,387,369, issued May 14, 2002), which is the national phase application of PCT Application No. PCT/US98/14520, filed Jul. 14, 1998, which claims priority of U.S. provisional application Ser. No. 60/052,910, filed Jul. 14, 1997; the contents of each application are incorporated by reference in their entireties.

FEDERALLY SPONSORED RESEARCH OR DEVELOPMENT

[Not Applicable]

BACKGROUND OF THE INVENTION

The present technology relates to the replacement, repair, and/or regeneration of cardiac tissue and muscle.

On a yearly basis, it is estimated over 300,000 Americans will die from congestive heart failure. The ability to augment weakened cardiac muscle would be a major advance in the treatment of cardiomyopathy and heart failure. Despite advances in the medical therapy of heart failure, the mortality due to this disorder remains high, where most patients die within one to five years after diagnosis.

A common heart ailment in the aging population is improper heart valve function, particularly the aortic valve. Mechanical replacement valves are widely used, but require the patient to continually take blood thinners. Valves obtained from cadavers and xenographs (porcine) are also frequently used to replace a patient's own tissue. Such valves are freeze-dried or chemically cross-linked using, for example, glutaraldehyde to stabilize the collagen fibrils and decrease antigenicity and proteolytic degradation. However, these valves remain acellular and often fail after several years due to mechanical strain or calcification. A replacement valve derived from a biocompatible material that would allow ingrowth of the appropriate host cells and renewal of tissue over time would be preferred.

Adult bone marrow is an accessible and renewable source of adult stem cells that can be greatly expanded in culture. For example, mesenchymal stem cells (MSCs) are multipotential cells that have been identified and cultured from avian and mammalian species including mouse, rat, rabbit, dog and human (See Caplan, 1991; Caplan et al. 1993; and U.S. Pat. No. 5,486,359). Isolation, purification and culture expansion of hMSCs is described in detail therein.

BRIEF SUMMARY OF THE INVENTION

In accordance with the present technology, adult bone marrow-derived stem cells are used to regenerate or repair striated cardiac muscle that has been damaged through disease or degeneration. Adult bone marrow-derived stem cells of the present technology have the capacity to differentiate into at least one cell type of each of the mesodermal, ectodermal, and endodermal lineages. For example, the cells can be induced to differentiate into cells of at least osteoblast, chondrocyte, adipocyte, fibroblast, marrow stroma, skeletal muscle, smooth muscle, cardiac muscle, endothelial, epithelial, hematopoietic, glial, neuronal or oligodendrocyte cell types, among others. Adult bone marrow-derived stem cells of the present technology are capable of differentiating into at least one cell type of at least one of the endodermal, ectodermal, or mesodermal embryonic lineages.

The present technology also provides a cell preparation comprising adult bone marrow derived stem cells in a dose effective to stimulate angiogenesis in the heart of a subject in need thereof. The stem cells can be capable of differentiating into at least one cell type of each of the endodermal, ectodermal, and mesodermal embryonic lineages. The effective dose of the cell preparation can comprise about 0.02 to about 150 milliliters of a pharmaceutically acceptable liquid medium. The stem cells can be at a concentration of about 10 to about 40 million cells per milliliter. The stem cells can have an induced expression of at least one cardiac specific marker, which can be, for example, myosin heavy chain, sarcoplasmic reticulum calcium ATPase, or connexin 43. The induced expression of the cardiac specific marker can result from (i) co-culturing the stem cells with cardiac cells, (ii) use of chemical fusigens to create heterokaryons of the stem cells with cardiomyocytes, (iii) incubating the stem cells with extracts of mammalian hearts, (iv) treatment of the stem cells with growth factors, differentiating agents, or both, (v) mechanical or electrical stimulation of the stem cells, or (vi) mechanical or electrical coupling of the stem cells with cardiomyocytes. The subject can be, for example, a myocardial infarction patient, an ischemic heart transplant patient, a congestive heart failure patient, or a coronary artery bypass graft patient. The cell preparation can be capable of improving ventricular ejection fraction (e.g., left ventricular ejection fraction) in the subject.

The present technology further provides a method of improving ventricular ejection fraction in a patient comprising administering to the patient bone marrow-derived stem cells in an amount effective to improve ventricular ejection fraction. Again, the ventricular ejection fraction can be left ventricular ejection fraction. The stem cells can be autologous or allogeneic to the patient. The stem cells can be administered in a pharmaceutically acceptable carrier, such as a liquid carrier. The stem cells can be administered directly to the heart of the patient, such as via a suitable catheter or during an open surgical procedure (e.g., coronary artery bypass graft surgery). The stem cells can be administered systemically, such as intravenously or intraarterially. The stem cells can be mesenchymal stem cells.

The present technology also provides a method of treating a patient having myocardial infarction or congestive heart failure and having reduced cardiac function comprising the step administering to the patient bone marrow-derived stem cells in an amount effective to improve cardiac function. The stem cells can be autologous or allogeneic to the patient. The stem cells can be administered in a pharmaceutically acceptable carrier, such as a liquid carrier. The stem cells can be administered directly to the heart of the patient, such as via a suitable catheter or during an open surgical procedure (e.g., coronary artery bypass graft surgery). The stem cells can be administered systemically, such as intravenously or intraarterially. The stem cells can be mesenchymal stem cells. The method can further comprise assessing cardiac function at a time after administering the stem cells. The assessment can comprise the step of measuring ventricular function, such as by measuring ventricular ejection fraction, ventricular end diastolic pressure, or ventricular wall motion. The method can also comprise measuring left ventricular ejection fraction.

Additionally, the present technology provides a method of augmenting ventricular function in a patient comprising administering to the heart of the patient a cell suspension, wherein the cell suspension comprises bone marrow-derived stem cells and a pharmaceutically acceptable liquid medium. The stem cells can be autologous or allogeneic to the patient. The suspension cells can be administered to the heart of the patient, such as via a suitable catheter or during an open surgical procedure (e.g., coronary artery bypass graft surgery). The stem cells can be mesenchymal stem cells. The patient can have, for example, a left ventricular ejection fraction of less than about 40%, or be suffering from congestive heart failure.

In accordance with the present technology adult bone marrow-derived stem cells, such as mesenchymal stem cells (MSCs), are used to regenerate or repair striated cardiac muscle that has been damaged through disease or degeneration. In certain embodiments, MSCs differentiate into cardiac muscle cells and integrate with the healthy tissue of the recipient to replace the function of the dead or damaged cells, thereby repairing and/or regenerating the cardiac muscle as a whole. Cardiac muscle does not normally have reparative potential. Adult bone marrow-derived stem cells are used, for example, in cardiac muscle repair and/or regeneration for a number of principal indications: (i) ischemic heart transplantations, (ii) therapy for congestive heart failure patients, (iii) prevention of further disease for patients undergoing coronary artery bypass graft, (iv) conductive tissue regeneration, (v) vessel smooth muscle regeneration, or (vi) valve regeneration. Adult bone marrow-derived stem cells are also used to integrate with tissue of a replacement heart valve to be placed into a recipient. For example, MSCs, preferably autologous, repopulate the valve tissue, thereby enabling proper valve function.

Cardiac muscle therapy using adult bone marrow-derived stem cells is based, for example, on the following sequence: harvest of stem cell-containing tissue, isolation/expansion of stem cells, administration by either implantation (including by catheterization) into the damaged heart (with or without a stabilizing matrix and biochemical manipulation) or systemic injection, and in situ formation of myocardium or repair of damaged myocardium. This approach is different from traditional tissue engineering, in which the tissues are grown ex vivo and implanted in their final differentiated form. Biological, bioelectrical and/or biomechanical triggers from the host environment may be sufficient, or under certain circumstances, may be augmented as part of the therapeutic regimen to establish a fully integrated and functional repair or regenerated tissue.

Accordingly, one aspect of the present technology provides a method for producing cardiomyocytes in an individual in need thereof which comprises administering to the individual a myocardium-producing amount of mesenchymal stem cells. The mesenchymal stem cells that are employed may be a homogeneous composition or may be a mixed cell population enriched in MSCs. Homogeneous human mesenchymal stem cell compositions are obtained by culturing adherent marrow or periosteal cells; the mesenchymal stem cells may be identified by specific cell surface markers which are identified with unique monoclonal antibodies. A method for obtaining a cell population enriched in mesenchymal stem cells is described, for example, in U.S. Pat. No. 5,486,359.

Adult stem cells can be obtained from a variety of sources, including bone marrow. For example, human mesenchymal stem cells can be obtained from bone marrow from a number of different sources, including plugs of femoral head cancellous bone pieces, patients with degenerative joint disease during hip or knee replacement surgery, and aspirated marrow from normal donors or oncology patients who have marrow harvested for future bone marrow transplantation. Harvested marrow can be prepared for cell culture by a number of different mechanical isolation processes depending upon the source of the harvested marrow (i.e., the presence of bone chips, peripheral blood, etc.) that are well known in the art. Exemplary culture media and culture conditions are identified in, for example, U.S. Pat. No. 5,486,359 and include media and conditions that allow for expansion, growth, and isolation of mesenchymal stem cells, without differentiation.

Cell preparations having greater than about 95%, usually greater than about 98%, of adult human bone marrow-derived stem cells can be achieved using techniques for isolation, purification, and culture expansion of stem cells. For example, isolated, cultured mesenchymal stem cells can comprise a single phenotypic population (about 95% or about 98% homogeneous) by flow cytometric analysis of expressed surface antigens. The desired cells in such composition can be identified, for example, by expression of a cell surface marker (e.g., CD73 or CD105) specifically bound by an antibody produced from hybridoma cell line SH2, ATCC accession number HB 10743, an antibody produced from hybridoma cell line SH3, ATCC accession number HB 10744, or an antibody produced from hybridoma cell line SH4, ATCC accession number HB 10745. Such antibodies selectively bind bone marrow-derived mesenchymal stem cells and, therefore, can be used to identify, quantify, isolate, or purify mesenchymal stem cells from bone marrow samples.

The administration of the cells can be directed to the heart, by a variety of procedures. Localized administration is preferred. The adult bone-marrow derived stem cells can be from a spectrum of sources including, in order of preference: autologous, allogeneic, or xenogeneic. There are several embodiments to this aspect, including the following.

In one embodiment of this aspect, the adult bone-marrow derived stem cells can be administered as a cell suspension in a pharmaceutically acceptable liquid medium for injection. Injection, in this embodiment, can be local, such as by administration directly into the damaged portion of the myocardium, or systemic, such as intravenously or intraarterially. Here, again, localized administration is preferred.

In another embodiment of this aspect, the adult bone-marrow derived stem cells, such as MSCs, are administered in a biocompatible medium which is, or becomes in situ at the site of myocardial damage, a semi-solid or solid matrix. For example, the matrix may be (i) an injectible liquid which "sets up" (or polymerizes) to a semi-solid gel at the site of the damaged myocardium, such as collagen and its derivatives, polylactic acid or polyglycolic acid, or (ii) one or more layers of a flexible, solid matrix that is implanted in its final form, such as impregnated fibrous matrices. The matrix can be, for example, Gelfoam (Upjohn, Kalamazoo, Mich.). The matrix holds the stem cells in place at the site of injury, and thus serves the function of "scaffolding". This, in turn, enhances the opportunity for the administered adult bone-marrow derived stem cells to proliferate, differentiate and eventually become fully developed cardiomyocytes. Although not wishing to be bound by any particular theory, it is believed that as a result of their localization in the myocardial environment they then integrate with the recipient's surrounding myocardium. These events likewise occur in the above liquid injectible embodiment, but this embodiment may be preferred where more rigorous therapy is indicated.

In another embodiment of this aspect, the adult bone marrow-derived stem cells are induced or genetically modified or engineered to express proteins of importance for the differentiation and/or maintenance of striated muscle cells. Some examples include growth factors (TGF-β, IGF-1, FGF), myogenic factors (myoD, myogenin, Myf5, MRF), transcription factors (GATA-4), cytokines (cardiotrophin-1), members of the neuregulin family (neuregulin 1, 2 and 3) and homeobox genes (Csx, tinman, NKx family). Also contemplated are genes that encode for factors that stimulate angiogenesis and revascularization (e.g., vascular endothelial growth factor (VEGF)). Any of the known methods for introducing DNA are suitable, however electroporation, retroviral vectors and adeno-associated virus (AAV) vectors are preferred.

Thus, in association with the embodiment of the above aspect using genetically engineered stem cells, the present technology also provides new and unique genetically engineered adult bone marrow-derived stem cells and tissue compositions to treat the above indications. The compositions can include genetically modified cells and unmodified cells in various proportions to regulate the amount of expressed exogenous material in relationship to the total number of cells to be affected.

The present technology also relates to the potential of MSCs to differentiate partially to the cardiomyocyte phenotype using in vitro methods. This technique can under certain circumstances optimize conversion of MSCs to the cardiac lineage by predisposing them thereto. This also has the potential to shorten the time required for complete differentiation once the cells have been administered.

BRIEF DESCRIPTION OF THE DRAWINGS

FIG. 1A shows the low magnification image of a rat heart which has been injected with dye labeled cells and later, a T-incision was made at the site. FIGS. 1A and 1B reveal the labeled MSCs in the ventricle wall viewed from the outer surface. FIG. 1C shows a cross-section of the ventricle wall and that the cells are present in the outer 1-2 mm of the 3 mm thick cardiac muscle.

FIG. 6A is a hematoxylin and eosin stained section, while FIG. 6B is a fluorescent image showing the mesenchymal stem cells (dark, or blue) and of smooth muscle actin (light, or green), wherein the section was contacted with an FITC-labeled monoclonal antibody against smooth muscle actin.

FIGS. 7A and 7D are hematoxylin and eosin stained sections. FIG. 7B is a fluorescent image of DAPI-labeled mesenchymal stem cells. FIG. 7C is a fluorescent image showing the presence of DAPI-labeled mesenchymal stem cells (dark, or blue) and of Factor VIII (light, or green), wherein the section was contacted with an FITC labeled monoclonal antibody against Factor VIII. FIG. 7E is a fluorescent image showing the presence of DAPI-labeled mesenchymal stem cells (dark, or blue), and of vascular endothelial growth factor (VEGF), wherein the section was contacted with an FITC-labeled monoclonal antibody against VEGF.

DETAILED DESCRIPTION OF PREFERRED EMBODIMENTS

Figure 1A:
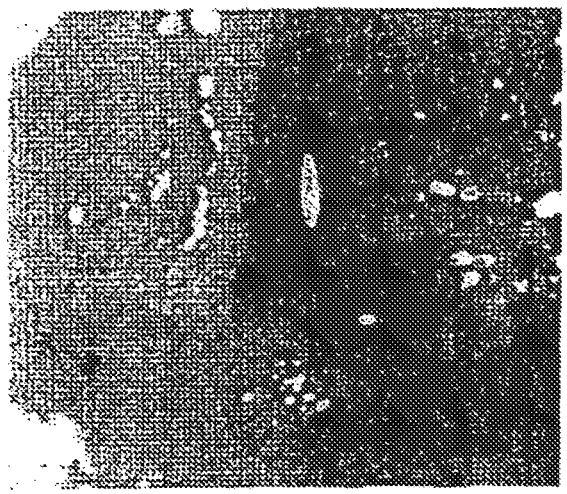
FIGS. 1A-1C show cardiac muscle injected, using a fine needle, with in vitro dye-labeled MSCs. The lipophilic dyes PKH26 (Sigma Chemical) or CM-DiI (Molecular Probes) were utilized to label MSCs prior to being introduced into animals. These dyes remain visible when the tissue site is harvested approximately 1-2 months later. Such dyes do not interfere with the differentiation of MSCs in in vitro assays.

It is believed that he proper environmental stimuli convert MSCs into cardiac myocytes. Differentiation of mesenchymal stem cells to the cardiac lineage is controlled by factors present in the cardiac environment. Exposure of MSCs to a simulated cardiac environment directs these cells to cardiac differentiation as detected by expression of specific cardiac muscle lineage markers. Local chemical, electrical and mechanical environmental influences alter pluripotent MSCs and convert the cells grafted into the heart into the cardiac lineage.

Early in embryonic development following the epithelia-mesenchyme transition, the presumptive heart mesenchyme from the left and right sides of the body migrate to the ventral midline. Here, interaction with other cell types induces continued cardiogenesis. In vitro conversion of MSCs to cardiomyocytes is tested by co-culture or fusion with murine embryonic stem cells or cardiomyocytes, treatment of MSCs with cardiac cell lysates, incubation with specific soluble growth factors, or exposure of MSCs to mechanical stimuli and electrical stimulation.

A series of specific treatments applicable to MSCs to induce expression of cardiac specific genes are disclosed herein. The conditions are effective on rat, canine and human MSCs. Treatments of MSCs include (1) co-culturing MSCs with fetal, neonatal and adult rat cardiac cells, (2) use of chemical fusigens (e.g., polyethylene glycol or sendai virus) to create heterokaryons of MSCs with fetal, neonatal and adult cardiomyocytes, (3) incubating MSCs with extracts of mammalian hearts, including the extracellular matrix and related molecules found in heart tissue, (4) treatment of MSCs with growth factors and differentiating agents, (5) mechanical and/or electrical stimulation of MSCs, and (6) mechanically and/or electrically coupling MSCs with cardiomyocytes. MSCs that progress towards cardiomyocytes first express proteins found in fetal cardiac tissue and then proceed to adult forms. Detection of expression of cardiomyocyte specific proteins is achieved using antibodies to, for example, myosin heavy chain monoclonal antibody MF 20 (MF20), sarcoplasmic reticulum calcium ATPase (SERCA1) (mAb 10D1) or gap junctions using antibodies to connexin 43.

Cardiac injury promotes tissue responses which enhance myogenesis using implanted MSCs. Thus, MSCs are introduced to the infarct zone to reduce the degree of scar formation and to augment ventricular function. New muscle is thereby created within an infarcted myocardial segment. MSCs are directly infiltrated into the zone of infarcted tissue. The integration and subsequent differentiation of these cells is characterized, as described above. Timing of intervention is designed to mimic the clinical setting where patients with acute myocardial infarction would first come to medical attention, receive first-line therapy, followed by stabilization, and then intervention with myocardial replacement therapy if necessary.

Of the four chambers of the heart, the left ventricle is primarily responsible for pumping blood under pressure through the body's circulatory system. It has the thickest myocardial walls and is the most frequent site of myocardial injury resulting from congestive heart failure. The degree of advance or severity of the congestive heart failure ranges from those cases where heart transplantation is indicated as soon as a suitable donor organ becomes available to those where little or no permanent injury is observed and treatment is primarily prophylactic.

The severity of resulting myocardial infarction as determined by the percentage of muscle mass of the left ventricle that is involved can range from about 5 to about 40 percent. This represents affected tissue areas, whether as one contiguous ischemia or the sum of smaller ischemic lesions, having horizontal affected areas from about 2 cm$^2$ to about 6 cm$^2$ and a thickness of from 1-2 mm to 1-1.5 cm. The severity of the infarction is significantly affected by which vessel(s) is involved and how much time has passed before treatment intervention is begun.

The mesenchymal stem cells used in accordance with the present technology are, in order of preference, autologous, allogeneic or xenogeneic, and the choice can largely depend on the urgency of the need for treatment. A patient presenting an imminently life threatening condition may be maintained on a heart/lung machine while sufficient numbers of autologous MSCs are cultured or initial treatment can be provided using other than autologous MSCs.

The MSC therapy of the present technology can be provided by several routes of administration, including the following. First, intracardiac muscle injection, which avoids the need for an open surgical procedure, can be used where the MSCs are in an injectable liquid suspension preparation or where they are in a biocompatible medium which is injectable in liquid form and becomes semi-solid at the site of damaged myocardium. A conventional intracardiac syringe or a controllable arthroscopic delivery device can be used so long as the needle lumen or bore is of sufficient diameter (e.g., 30 gauge or larger) that shear forces will not damage the MSCs. The injectible liquid suspension MSC preparations can also be administered intravenously, either by continuous drip or as a bolus. During open surgical procedures, involving direct physical access to the heart, all of the described forms of MSC delivery preparations are available options.

As a representative example of a dose range is a volume of at least about 20 μl, preferably at least about 500 μl, of injectible suspension containing about 10 to about 40×10$^6$ MSCs/ml. The concentration of cells per unit volume, whether the carrier medium is liquid or solid remains within substantially the same range. The amount of MSCs delivered will usually be greater when a solid, "patch" type application is made during an open procedure, but follow-up therapy by injection will be as described above. The frequency and duration of therapy will, however, vary depending on the degree (percentage) of tissue involvement, as already described (e.g., about 5 to about 40% left ventricular mass).

In cases having about 5% to about 10% tissue involvement, it is possible, for example, to treat with as little as a single administration of about one million MSCs in about 20 to about 50 μl of injection preparation. The injection medium can be any pharmaceutically acceptable isotonic liquid. Examples include phosphate buffered saline (PBS), culture media such as Dulbecco's Modified Eagle's Medium (DMEM; preferably serum-free), physiological saline or about 5% dextrose in water (D5W).

In cases having more in a range of about 20% tissue involvement severity level, multiple injections of about 20 to about 50 μl (about 10 to about 40×10$^6$ MSCs/ml) are envisioned. Follow-up therapy may involve additional dosings.

In very severe cases, for example in a range of about 40% tissue involvement severity level, multiple equivalent doses for a more extended duration with long term (up to several months) maintenance dose aftercare may well be indicated and are envisaged in accordance with the practice of the present technology.

When given intravenously, the mesenchymal stem cells may be administered in at least about 20 μl, preferably at least about 500 μl, and up to about 150 ml of a suspension containing about 10 to about 40×10$^6$ MSCs/ml. In one embodiment, from about 40 ml to about 150 ml of a suspension containing about 10 to about 40×10$^6$ MSCs/ml is given intravenously.

Applicants also have discovered that the mesenchymal stem cells may stimulate and/or promote angiogenesis in the heart and/or repair or regenerate blood vessels of the heart. Thus, in accordance with another aspect of the present technology, there is provided a method of stimulating or promoting angiogenesis in the heart, and/or of repairing or regenerating blood vessels of the heart of an individual by administering to the individual mesenchymal stem cells in an amount effective to stimulate or promote angiogenesis, and/or repair or regenerate blood vessels of the heart. The mesenchymal stem cells may be administered as a cell suspension in a pharmaceutically acceptable liquid medium such as described herein, or in a biocompatible medium which is, or becomes in situ at the site of myocardial damage, a semi-solid or solid matrix, also as described herein.

The mesenchymal stem cells may be allogeneic, autologous, or xenogeneic, and may be administered in dosages such as those described herein.

When the mesenchymal stem cells are administered as a cell suspension in a pharmaceutically acceptable liquid medium for injection, they may be administered locally, such as by administration directly into the damaged portion of the heart by, for example, an endocardial catheter, or they may be administered systemically, such as by intravenous or intraarterial administration.

Adult bone marrow-derived stem cells, including mesenchymal stem cells, provide for the repair and/or regeneration of existing blood vessels of the heart, as well as promote angiogenesis (i.e., the formation of new blood vessels of the heart). Blood vessels which may be repaired or regenerated, as well as new blood vessels which may be formed, include arteries (including arterioles), and veins, as well as capillaries.

The present technology is further illustrated, but not limited, by the following examples.

Example 1

Implantation of MSCs in Normal Cardiac Muscle

In using MSCs, it is desirable, for example, to maintain cell-cell contact in vivo for the conversion of MSCs to the muscle lineage. Environmental signals identified above act in concert with mechanical and electrical signaling in vivo to lead to cardiac differentiation.

Primary human MSCs (hMSCs) are introduced into athymic rat myocardial tissue by direct injection. The integration of implanted cells, their subsequent differentiation, formation of junctions with cardiac cells, and their long-term survival are characterized with light microscopy, histology, confocal immunofluorescence microscopy, electron microscopy and in situ hybridization.

Whether human MSCs are appropriately grafted into cardiac muscle of athymic rats (strain HSD:RH-RNU/RNU), which lack the immune responses necessary to destroy many foreign cells, is also examined.

Rat MSCs are grafted into the heart muscles of rats. To analyze the injected cells over several weeks and to minimize the possibility of immune system rejection, MSCs are harvested from Fisher 344 rats, the same inbred strain (identical genotype) as the intended MSC recipients.

The MSCs can be marked in a variety of ways prior to their introduction into the recipient. This makes it possible to trace the fate of the MSCs as they proliferate and differentiate in the weeks following the MSC implant. Several methods are utilized to identify positively the injected cells: membrane lipid dyes PKH26 or CM-Dil and genetic marking with adeno-associated virus (AAV) or retroviruses, such as Moloney murine leukemia virus expressing green fluorescent protein (GFP) or galactosidase. PCR also is used to detect the Y chromosome marker of male cells implanted into female animals. The dye-labeled cells are detected readily and offer the simplest method to directly follow the injected cells. This method is reliable for times out to at least 4 weeks. On the day of introduction to recipient animals, MSCs are trypsinized and labeled with CM-Dil according to the recommendations of the manufacturer (Molecular Probes). Subconfluent monolayer cultures of MSCs are incubated with 5 mM CM-Dil in serum-free medium for 20 minutes, trypsinized, washed twice in excess dye-free medium, and utilized for injection.

Alternatively, MSCs are genetically marked prior to injections, such as by using AAV-GFP vector. This vector lacks a selectable marker, but mediates a high-level expression of the transduced genes in a variety of post-mitotic and stem cell types. Recombinant AAV-GFP is added to low density monolayers of MSCs in low serum. Following a four hour incubation at 37° C., the supernatant is removed and replaced with fresh media. At 96 hours after transduction, cells are assayed for green fluorescent protein (GFP) activity. Typically 50% of the cells express the transduced gene. Unselected MSCs on a clonal line, isolated by limiting dilution, are utilized for injection. Cells are collected following trypsin treatment, washed and used at high concentrations for injection (10 to 100 million cells per ml).

Figure 1B:
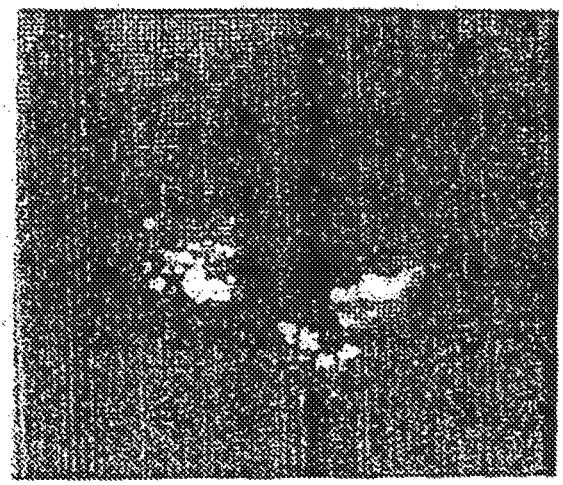
Figure 1C:
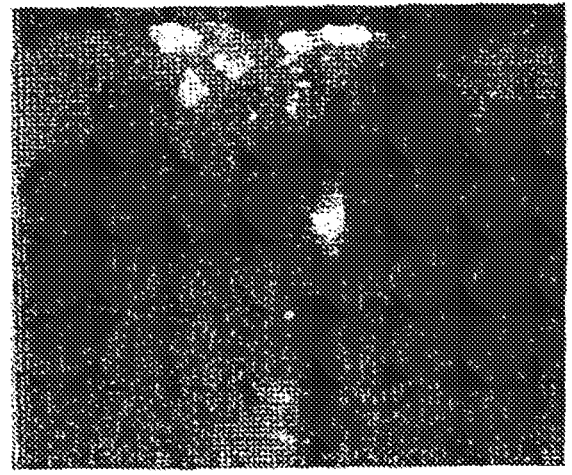

To test whether the hMSCs became cardiomyocytes in the heart environment, the hearts of ten week old athymic rats were injected with dye labeled or GFP-labeled human MSCs. All procedures were performed under strict sterile conditions. The animals were placed in a glass jar containing a methoxyflurane anesthesia soaked sponge. Under sterile conditions, a 20 mm anterior thoracotomy was performed, and following visualization of the left ventricle, about 10 µl of the cell suspension, containing about 10,000 to about 100,000 MSCs in serum-free medium were injected into the left ventricular apex using a 30 gauge needle. The procedure was performed rapidly with endotracheal intubation and mechanical ventilation assist. The incision was closed with sutures. Ventilation assist was normally unnecessary after a short period following chest closure. FIG. 1A shows the low magnification image of a rat heart which was injected with dye labeled cells and later, a T-incision had been made at the site to reveal the injected cells in the ventricle wall. FIG. 1A is a gross photo of the incised heart. FIGS. 1B and 1C reveal the labeled MSCs in the ventricle wall. FIG. 1C shows that the cells were present in the outer 1 to 2 mm of the 3 mm thick rat cardiac muscle.

When sacrificed, the heart is removed, examined by light microscopy for the presence of vascular thrombi or emboli, paraffin-embedded, and sectioned. The histology of serial sections is examined to determine the fate of dye-stained cells. Sections then are tested for immunohistochemical markers of cardiac muscle in the areas of the introduced MSCs to ascertain whether donor MSCs have differentiated into cardiomyocytes in vivo. Implantation surgeries are carried out on animals to be sacrificed at 1, 2, 4, and 6 weeks (4 animals at each time point) and the hearts which received implants are analyzed histologically and immunologically.

For phenotypic characterization, the hearts are removed and processed for histology by immunofluorescence microscopy. Differentiation of MSCs is determined by the immunofluorescence localization of sacomeric myosin heavy chain, SERCA1 and phospholamban. The sequence-specific antibody to gap junction protein connexin 43, which is commercially available (Zymed, San Francisco, Calif.) and detects gap junctions in cardiac tissue is also used.

MSCs are also implanted in biomatrix materials to determine if enhanced grafting would be observed, such as Type I collagen. The MSCs are mixed rapidly with the matrix in a small volume and injected into the ventricle wall. The biomatrices are used at concentrations of 0.1 mg/ml or greater. For example, the biomatrices may be used at concentrations of 1 to 3 mg/ml containing 10 to 100 million cells/ml. The tissue is analyzed at times of 1, 2, 4, and 6 weeks as described above.

Example 2

Regeneration of Heart Valves Using MSCs

Xenograft or homograft valves are made acellular by freeze-drying, which leads to cellular death, or by enzymatic treatment followed by detergent extraction of cells and cell debris. This latter approach was taken by Vesely and coworkers with porcine valves to be repopulated with dermal or aortic fibroblasts. Curtil, et al. 1997 used a freeze-dried porcine valve and attempted repopulation of the valve with human fibroblasts and endothelial cells. These studies were preliminary and limited to short term studies in vitro.

The acellular valve to be populated by autologous hMSCs is incubated with culture expanded hMSCs in a tumbling vessel to ensure loading of cells to all valve surfaces. The valve is then cultured with the hMSCs for 1-2 weeks to allow the hMSCs to infiltrate and repopulate the valve. Within the culture vessel, the valve is then attached to a pump to allow the actuation of the valve leaflets and simulate the pumping motion present in the body. The valve is maintained in the pumping mode for 1-2 weeks to allow cellular remodeling associated with the stresses of the pumping action. Once sufficient cellular remodeling has occurred, the valve is implanted into the body of the patient.

Another embodiment of this aspect of the present technology is to first repopulate the valve with hMSCs and to later incubate the valve tissue during the pumping stage with autologous smooth muscle cells isolated from a vascular graft which will line the lumen of the valve.

Example 3

MSC Engraftment in Rat MI Model: Direct Injection vs. Systemic Delivery

Myocardial infarction was produced in Fisher rats as follows:

Fisher rats were given a cocktail of Ketamine/Xylazine/Acepromazine (8.5 mg/1.7 mg/0.3 mg I.P.) The depth of anesthesia was assessed using a toe-pinch and eye-blink reflexes. When a surgical plane of anesthesia was achieved, endotracheal intubation was performed and the animal placed on 1.0% Isoflurane. Positive-pressure breathing was provided throughout the procedure by means of the Engler ADS 1000 small animal ventilator. A left thoracotomy was performed and the pericardium opened. A 6-0 silk ligature snare was then placed around the left anterior descending (LAD) coronary artery at a location distal to the first diagonal branch. A brief (30 sec) LAD test occlusion is performed to insure that a modest region of ischemia is produced, involving a limited region of the anterior free wall and septum. Ischemia is confirmed by characteristic ECG changes, ventricular dyskinesia and regional cyanosis. Myocardial infarction is then produced by occluding the LAD for a period of 45 minutes. At the completion of the 45 minute period, the snare is removed and reperfusion visually confirmed. The chest was then closed by approximating the ribs and all associated musculature. The Isoflurane is turned off, the animal removed from the ventilator and extubated.

Figure 2A:
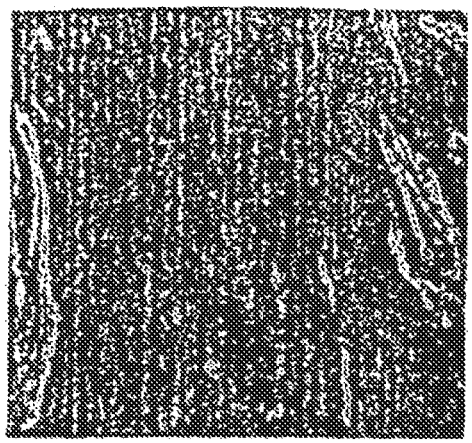
FIG. 2. Comparison of MSC engraftment when delivered to rats via direct cardiac injection (Panel A) or tail vein (Panel B). Confocal images were obtained in hearts harvested approximately 4 weeks post-implantation.
Figure 2B:
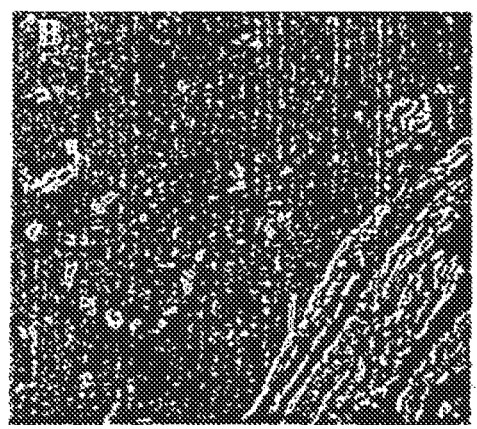

Panel A of FIG. 2 shows engraftment of MSCs in the heart following direct injection into the heart. In these experiments, $2\text{-}4\times10^6$ allogeneic rat MSCs were implanted into the area of necrosis by direct injection.

Panel B of FIG. 2 shows that tail vein injection results in cardiac engraftment.

These animals received MSCs via the tail vein. Injection of the allogeneic cell suspension occurred when the animals had stabilized, and a normal cardiac rhythm had been reestablished; usually within 15 minutes of reperfusion. At that time approximately $5\times10^6$ MSCs in a 0.5 milliliter suspension were injected slowly into the tail vein.

Example 4

Administration of MSCs Following MI Improves Ventricular Function

Swine are sedated with 1000 mg ketamine IM and brought into the lab. Intravenous access is established via an ear vein and the animals anesthetized with nembutal. Swine then are intubated, ventilated with 1.0-1.5% isoflurane, and prepped for surgery. ECG leads and rectal temperature probes are placed and the animal is draped to create a sterile field. A midline sternotomy is performed and the heart suspended in a pericardial cradle. A tygon catheter is placed in the apex of the left ventricle and sutured in place to measure ventricular pressure throughout the cardiac cycle. The left anterior descending (LAD) coronary artery is dissected free just distal to the first diagonal branch. A brief (30 sec) occlusion of the coronary artery is performed to identify the regions of ischemia (identified by the extent of cyanosis). Four piezoelectric crystals then are placed within regions destined for infarction.

At the completion of the surgical instrumentation a 15 minute stabilization period is allowed prior to obtaining baseline recordings. Following these recordings, the LAD there is occluded for a period of 60 minutes to produce myocardial infarction. Lidocaine (local anesthetic and antiarrhythmic) is administered at this time to reduce the incidence of ventricular fibrillation (2 mg/kg i.v. bolus plus 0.5 mg/min iv drip). Recordings of left ventricular pressure and regional contractile function are again obtained at 10 and 50 minutes of ischemia. Extensive cyanosis within the ischemic bed was noticed following 50 minutes of ischemia.

At the completion of the 60 minute period of ischemia, the snare is released and reperfusion established. Care is taken to ensure that perfusion is reestablished and that the isolated region of the LAD is not in spasm. At this time the leads (sono leads and LV catheter) are externalized, and the chest closed in layers. A chest tube is placed to reestablish a negative intrapleural pressure (tube is pulled 24 hrs later). The isoflurane is then turned off, and the animal is extubated and allowed to recover.

One set of infarcted swine was treated with allogeneic mesenchymal stem cells and another set (control) did not receive such treatment. The animals were examined using echocardiography. In the mesenchymal stem cell treatment, a 10 ml MSC suspension was drawn up into several 3 cc syringes using an 18 g needle. The needle was switched to a 30 g for delivery. Implantation was accomplished in the open chest setting. The needle was advanced to the mid-wall level, and 0.5 mls of cells were injected. This same procedure was performed approximately 20 times throughout the damaged area. Care was taken to provide cells to the entire apical anterior wall, as well as the septum. At the completion of the implantation procedure, the chest was closed and the animal allowed to recover.

Figure 3A:
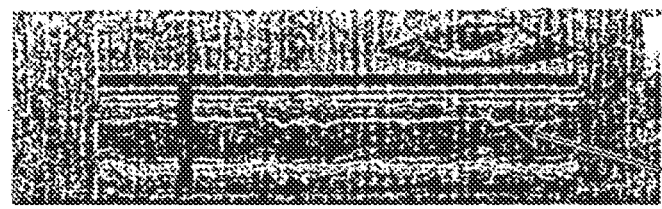
FIG. 3 shows images indicative of anterior wall motion in infarcted swine hearts that received no treatment and those that were treated with allogeneic MSCs.
Figure 3B:
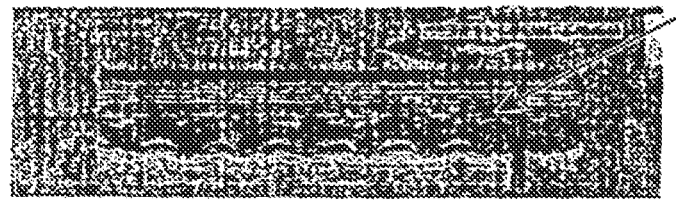
Figure 4A:
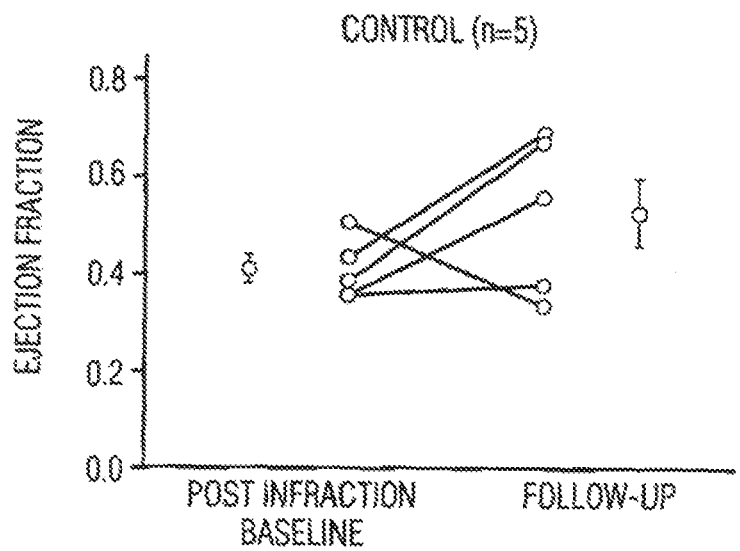
FIG. 4 shows graphs of ejection fraction (upper panels) measured in infarcted swine hearts that received no treatment and those that were treated with MSCs, and graphs of global wall motion (lower panels) in infarcted swine hearts that received no treatment, and those that were treated with MSCs.
Figure 4B:
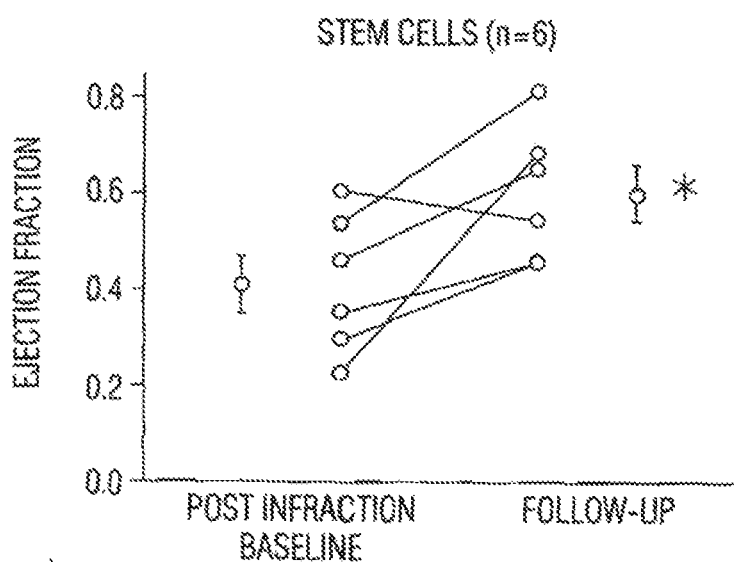
Figure 4C:
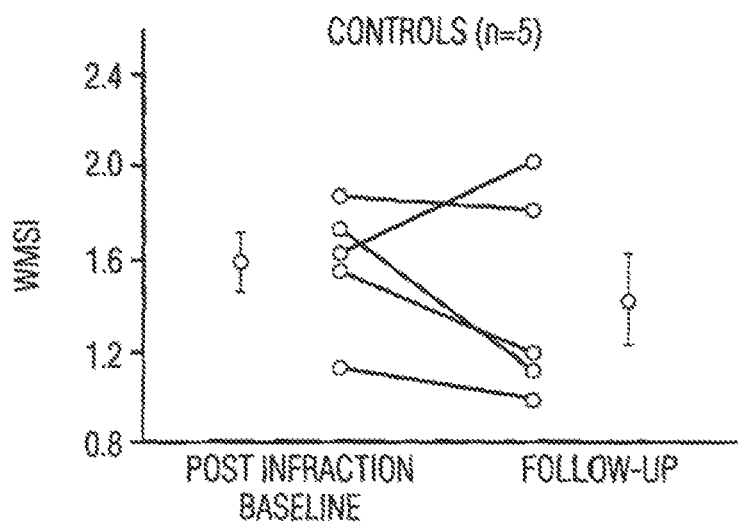
Figure 4D:
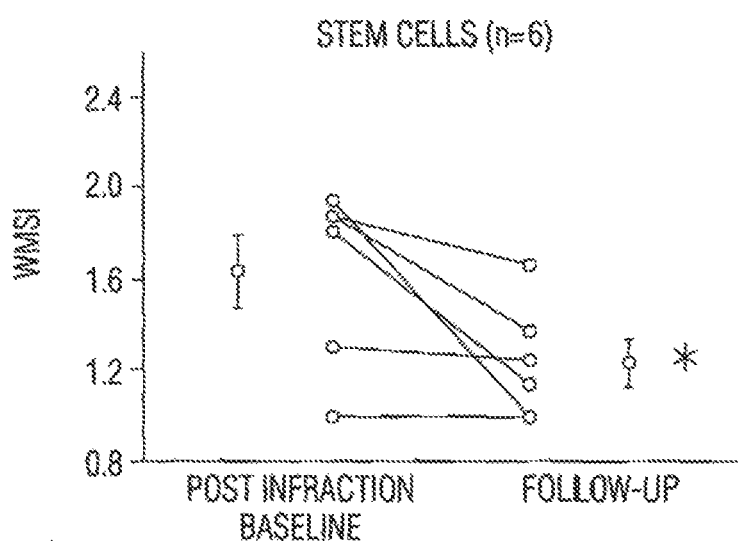

FIG. 3 contains "m-mode" images obtained in a control and an MSC treated animal. The image illustrates wall motion in a selected plane over time (moving left to right). The infarcted region of myocardium, consisting primarily of anterior LV free wall, is the structure highlighted by the arrows. That segment of myocardium is essentially akinetic in the control image, indicative of severe infarction/injury. While not quantifiable, there is improved anterior wall motion in the animal treated with allogeneic MSCs.

Echocardiography was used to measure the ejection fraction, a measure of global pump efficiency (a normal ejection fraction of 70% indicates that 70% of the LV volume is pumped with each beat of the heart; EF<40% is indicative of heart failure). Ejection fraction data is shown in the upper panels of FIG. 4. Control animals demonstrated no significant improvement in EF over the course of the study. In contrast, a statistically significant improvement in cardiac pump function was observed in MSC treated animals (right panel).

A similar graph was used to represent wall motion score index (lower panels of FIG. 4). In this analysis, 17 segments of the left ventricle were examined for wall motion and scored on a scale of 1-5, with 1 representing "normal" wall motion. These segments, comprising all areas of the ventricle, can then be averaged to gather an index of global wall motion (i.e., global function). As with ejection fraction, no significant improvement in wall motion was observed in control animals over time. MSC treated animals showed consistent and significant improvements in wall motion scores over time (right panel).

Figure 5:
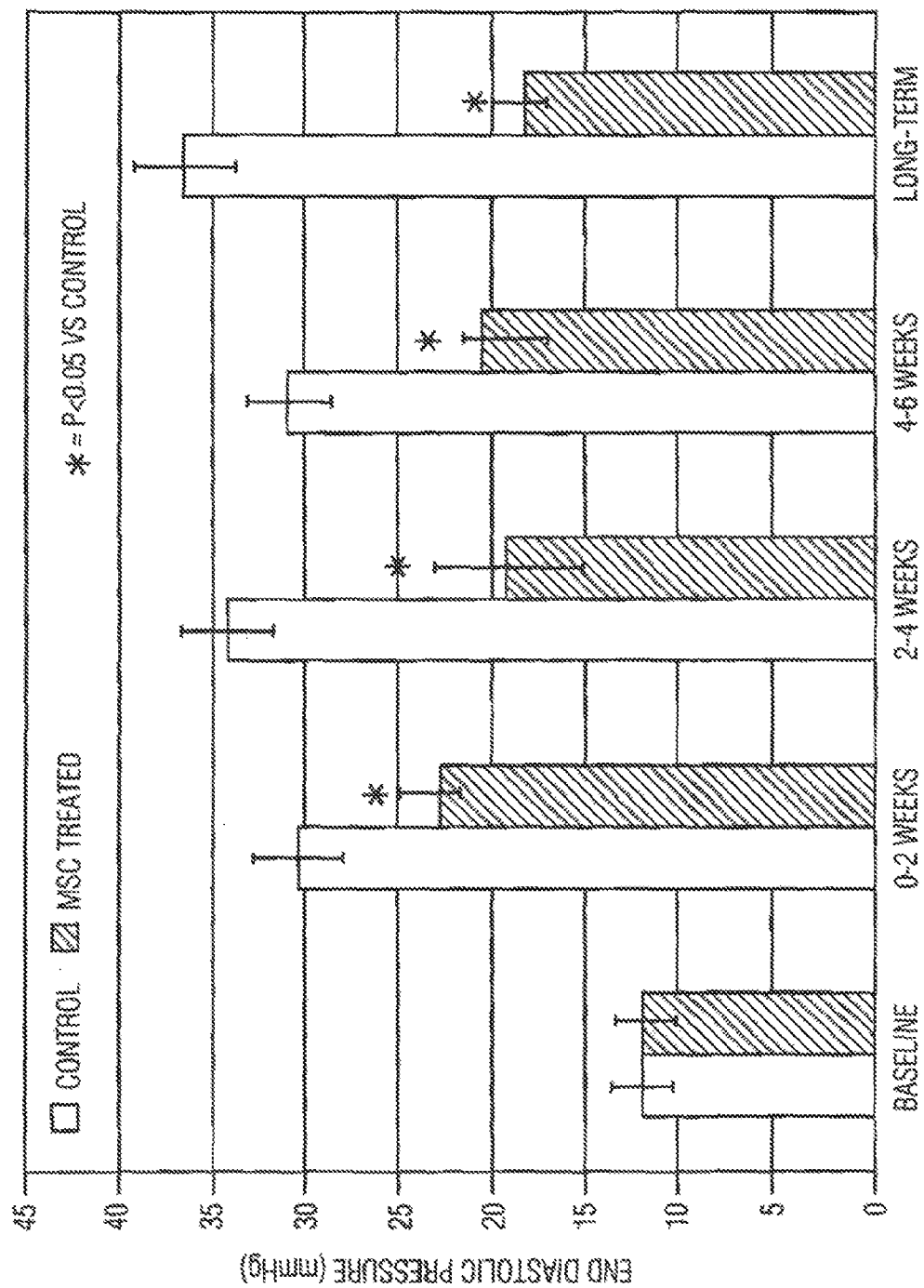
FIG. 5 is a graph of end diastolic pressure in infarcted swine hearts that received no treatment and those that were treated with MSCs.

Further evidence for improved cardiac function with MSC treatment is found when end diastolic pressure (EDP) is examined. When cardiac pump function is reduced following infarction, a pathologic increase in left ventricular EDP is observed. This increase in EDP is a clinically relevant finding that is often predictive of the progression to heart failure following infarction. As shown in FIG. 5, the EDP of control swine rose from approximately 12 to 35 mmHg in the 6 months following infarction. The rise in EDP in animals treated with MSCs of the present technology was significantly attenuated at all time points examined post-infarction.

Example 5

Administration of MSCs Prevents and/or Reverses Congestive Heart Failure Following MI Pathologic ventricular remodeling following myocardial infarction is a major cause of heart failure. It was previously demonstrated that autologous mesenchymal stem cells (MSC) augment local systolic wall thickening and prevent pathologic wall thinning. Based on in vitro studies, it was hypothesized that MSCs may be immuno-privileged, and that implantation of allogeneic MSCs could prevent pathologic remodeling and improve cardiac performance in a swine model of myocardial infarction. Piezoelectric crystals and an LV catheter were implanted in domestic swine prior to a 60' LAD occlusion to produce infarction. Following reperfusion, treated animals (n=7) were injected with allogeneic DiI-labeled MSCs ($2 \times 10^8$ cells in 9 ml) throughout the region of infarction. Control (CON, n=6) received vehicle injections. Allogeneic donor MSCs were previously isolated from swine iliac crest bone marrow, expanded in culture, and cryopreserved until the time of implantation. Hemodynamic parameters and regional wall motion were evaluated in conscious animals bi-weekly using trans-thoracic echocardiography and sonomicrometry. Animals were sacrificed at various time points (6-24 weeks) and tissue harvested for histological examination.

It was observed that implantation of allogeneic MSCs was not associated with ectopic tissue formation, significant inflammatory response or any adverse clinical event. Robust engraftment of allogeneic MSCs was observed in all treated animals. Furthermore, engrafted MSCs were found to express numerous muscle specific proteins, and exhibited morphological changes consistent with myogenesis. A marked improvement in both ejection fraction (55±9.4% vs 32.5±12.5% in CON) and global wall motion score (1.45±0.15 vs 2.1±0.2 in CON) was observed in treated animals at 10 weeks post-MSC implantation. Systolic wall thickening and diastolic wall thickness were also augmented in MSC treated animals. Because no significant difference in infarct size or cardiac loading was noted between groups, improvements in cardiac function are likely attributable to MSC implantation. In conclusion, this example suggests that implantation of allogeneic MSCs at reperfusion may be an effective therapeutic option to prevent or reverse the progression to heart failure following infarction.

The above examples illustrate that mesenchymal stem cells augment ventricular function, as shown, for example by improved cardiac ejection fraction and global wall motion.

Example 6

MSCs Repair and/or Regenerate Blood Vessels

A pig was subjected to a 60 minute LAD occlusion to produce infarction as described in Example 5. Three days after the infarction, $200 \times 10^6$ diaminopropidium iodide (DAPI)-labeled allogeneic mesenchymal stem cells were administered to the left venticular wall by endocardial catheter as 20 separate injections of $10 \times 10^6$ cells each in 0.5 ml physiological saline. DAPI is a nuclear stain which emits a strong blue fluorescence and aids in the identification of implanted cells.

Eight weeks after administration of the mesenchymal stem cells, the pig was sacrificed, and the heart was harvested for histological examination. Sections were subjected to hematoxylin and eosin staining, or to fluorescence imaging after being contacted with an FITC-labeled monoclonal antibody against smooth muscle actin.

Figure 6A:
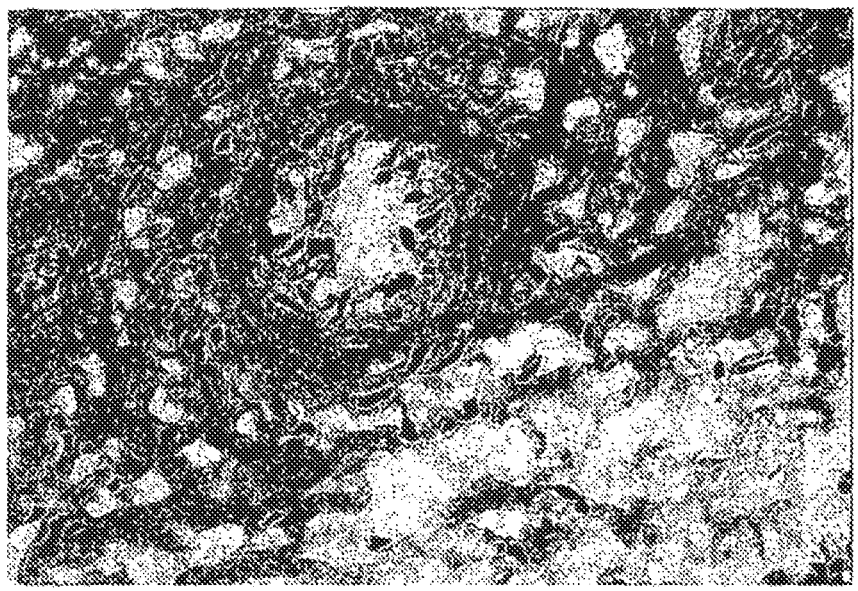
FIGS. 6A and 6B show sections of an infarcted region of a pig heart at 8 weeks after being treated with DAPI-labeled mesenchymal stem cells. Both figures show the presence of blood vessels in the infarcted region.

The hematoxylin and eosin image (FIG. 6A) clearly illustrates the presence of blood vessels within a generalized region of myocardial necrosis.

Figure 6B:
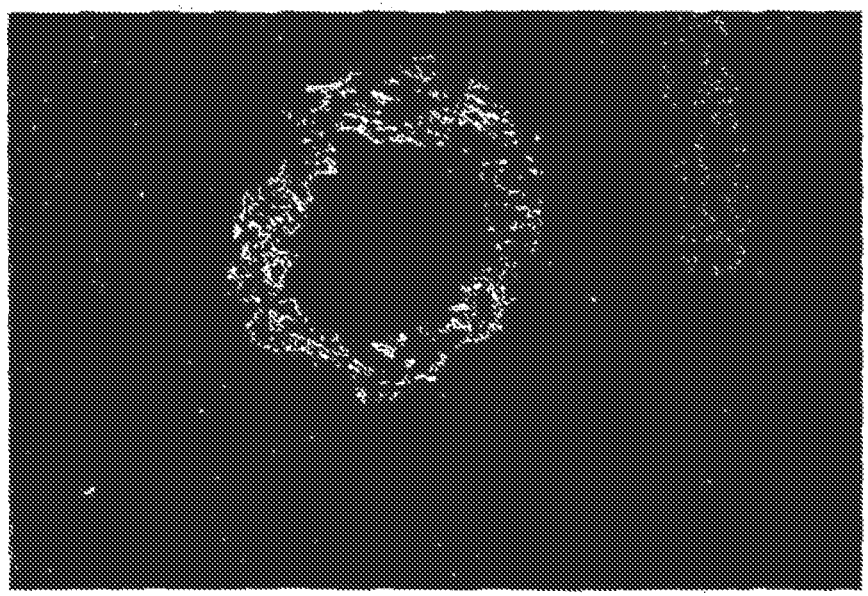

As shown in FIG. 6B, DAPI-labeled cells can be seen throughout the section; however, a localization of implanted MSCs can be identified readily. These MSCs surround, and are associated with, the blood vessels.

As shown in FIG. 6B, the lighter, or green, fluorescence indicates the presence of the FITC-labeled monoclonal antibody against smooth muscle actin, thus indicating the presence of a blood vessel. Also present in FIG. 6B are DAPI-labeled (blue) MSCs localized within such vessel, and which are associated intimately with the smooth muscle layer of the vessel. Thus, the MSCs are involved in the repair or regeneration of blood vessels of the heart.

Example 7

Cardiac Engrafted MSCs Express Angiogenic Proteins

A pig was subjected to a 60 minute LAD occlusion to produce infarction as described in Example 5. Three days after the infarction; the pig was given $200 \times 10^6$ diaminopropidium iodide (DAPI)-labeled allogeneic mesenchymal stem cells as 20 separate injections of $10 \times 10^6$ cells in 0.5 ml physiological saline into the left ventricular wall by endocardial catheter as described in Example 6.

Twelve weeks after administration of the mesenchymal stem cells, the pig was sacrificed, and the heart was harvested for histological examination. Sections were subjected to hematoxylin and eosin staining, or to fluorescence imaging after being contacted with an FITC-labeled monoclonal antibody against Factor VIII (Von Willebrand Factor) or an FITC-labeled monoclonal antibody against vascular endothelial growth factor (VEGF).

Figure 7A:
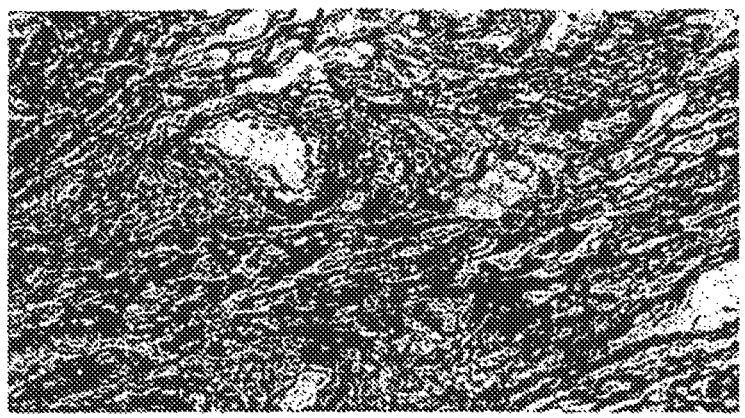
FIGS. 7A through 7E show sections of an infarcted pig heart at 12 weeks after being treated with DAPI-labeled mesenchymal stem cells. The figures show the presence of blood vessels in the infarcted region.
Figure 7B:
Figure 7C:
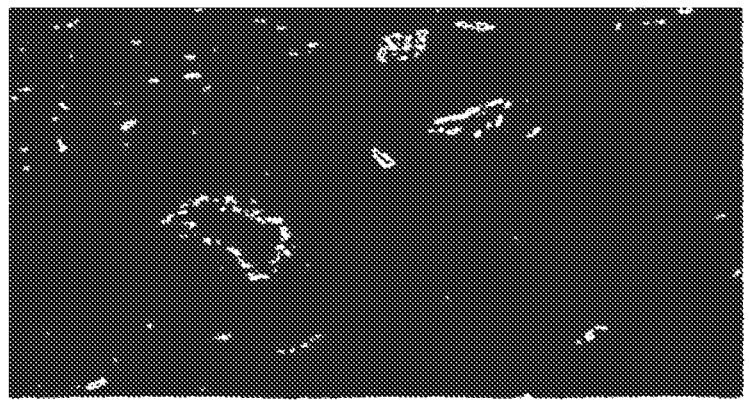
Figure 7D:
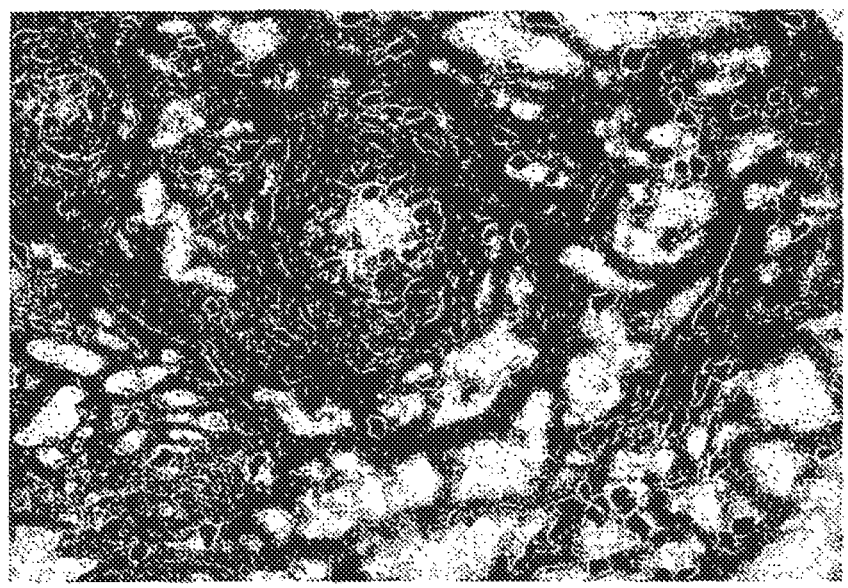

As shown in the hematoxylin and eosin images of FIGS. 7A and 7D, the presence of blood vessels within a region of generalized myocardial necrosis is illustrated.

Figure 7E:
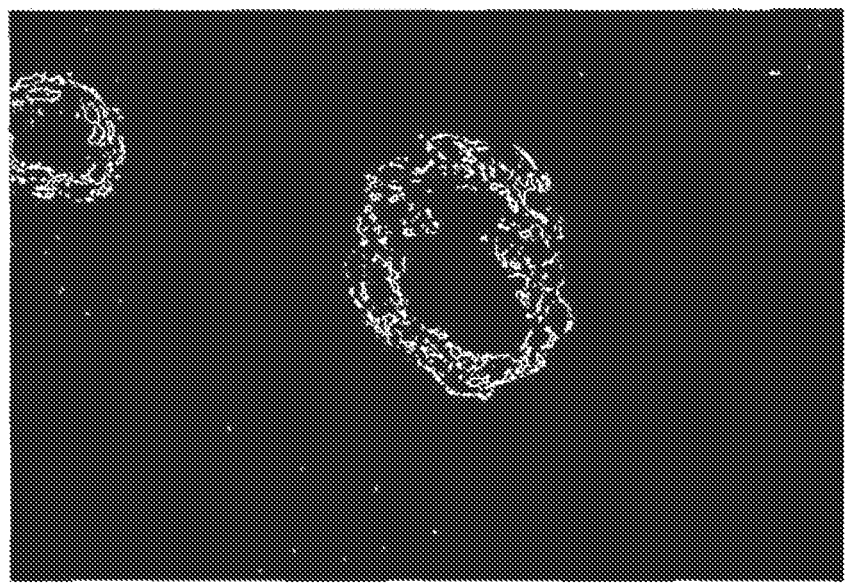

In the fluorescent images of FIGS. 7B, 7C and 7E, DAPI labeled cells can be seen throughout the sections; however, localizations of MSCs can be identified which surround and are associated intimately with the smooth muscle layer of the blood vessels. Light, or green, fluorescence indicates the presence of FITC-labeled monoclonal antibody against Factor VIII (FIG. 7C) or against VEGF (FIG. 7E).

Thus, it has been shown that the implanted MSCs express Factor VIII and VEGF, which are indicative of angiogenesis. These proteins are not expressed by cultured MSCs, but are expressed only after several weeks in the cardiac environment.

The disclosure of all patents and publications (including published patent applications) are hereby incorporated by reference in their entireties to the same effect as if each patent and publication were individually and specifically incorporated by reference.

It is to be understood, however, that the scope of the present technology is not to be limited to the specific embodiments described above. The technology may be practiced other than as particularly described and still be within the scope of the accompanying claims.

The invention claimed is:

1. A method of treating a patient having myocardial infarction or congestive heart failure and having reduced cardiac function comprising the step of: administering to the patient adult human allogeneic mesenchymal stem cells in an amount effective to improve cardiac function.

2. The method of claim 1, wherein the adult human allogeneic mesenchymal stem cells are administered intravenously or intraarterially.

3. The method of claim 1, further comprising the step of assessing cardiac function at a time after administering the adult human allogeneic mesenchymal stem cells, wherein the assessing comprises measuring at least one of left ventricular ejection fraction, ventricular end diastolic pressure, or ventricular wall motion.

4. The method of claim 3, wherein the assessing comprises measuring left ventricular ejection.

5. The method of claim 3, wherein the assessing comprises measuring ventricular end diastolic pressure.

6. The method of claim 3, wherein the assessing comprises measuring ventricular wall motion.

7. The method of claim 1, wherein the myocardial infarction involves about 5 percent to about 40 percent of muscle mass of the left ventricle.

8. The method of claim 1, wherein the adult human allogeneic mesenchymal stem cells are administered in a pharmaceutically acceptable liquid carrier.

9. The method of claim 8, wherein the pharmaceutically acceptable carrier comprises an isotonic liquid.

10. The method of claim 9, wherein the isotonic liquid comprises phosphate buffer saline, physiological saline, culture medium, or 5% dextrose in water.

11. The method of claim 9, wherein the pharmaceutically acceptable carrier comprises phosphate buffer saline.

12. The method of claim 1, wherein the adult human allogeneic mesenchymal stem cells are administered in a suspension containing about $10 \times 10^6$ to about $40 \times 10^6$ mesenchymal stem cells per ml.

13. The method of claim 12, wherein the cell suspension is administered in an amount of about 20 µl to about 150 µl.

14. The method of claim 12, wherein the cell suspension is administered in an amount of at least about 20 µl.

15. The method of claim 12, wherein the cell suspension is administered in an amount of at least about 150 µl.

* * * * *